United States Patent [19]

Raible

[11] 4,349,021
[45] Sep. 14, 1982

[54] ATRAUMATIC BLOOD ACCESS DEVICE VALVE

[75] Inventor: Donald A. Raible, Santa Ana, Calif.

[73] Assignee: Bentley Laboratories, Irvine, Calif.

[21] Appl. No.: 158,063

[22] Filed: Jun. 9, 1980

[51] Int. Cl.³ .............................................. A61M 5/00
[52] U.S. Cl. .................................. 128/214 R; 128/274
[58] Field of Search ................. 128/214 R, 274, 1 R, 128/348, 350 R, 214 B; 3/1

[56] References Cited

U.S. PATENT DOCUMENTS

| | | | |
|---|---|---|---|
| 4,092,983 | 6/1978 | Slivenko | 128/214 R |
| 4,108,173 | 8/1978 | Slivenko et al. | 128/214 R |
| 4,108,174 | 8/1978 | Slivenko | 128/214 R |
| 4,164,221 | 8/1979 | Bentley et al. | 128/274 |

Primary Examiner—Kyle L. Howell
Assistant Examiner—T. J. Wallen
Attorney, Agent, or Firm—Lyon & Lyon

[57] ABSTRACT

A valving mechanism for use within a blood passageway of a blood access device. The valving mechanism includes a plugging means and a valve chamber for receiving the plugging means when it is removed from its seat in the blood passageway. The valving mechanism also includes a retaining element adapted to slidably engage the valve chamber and an external rim of the blood access device for securing the valve chamber and blood access device. When the valve chamber is not in use, a retaining cap and retaining cap ring are used to secure the plugging means within the blood access device passageway.

10 Claims, 8 Drawing Figures

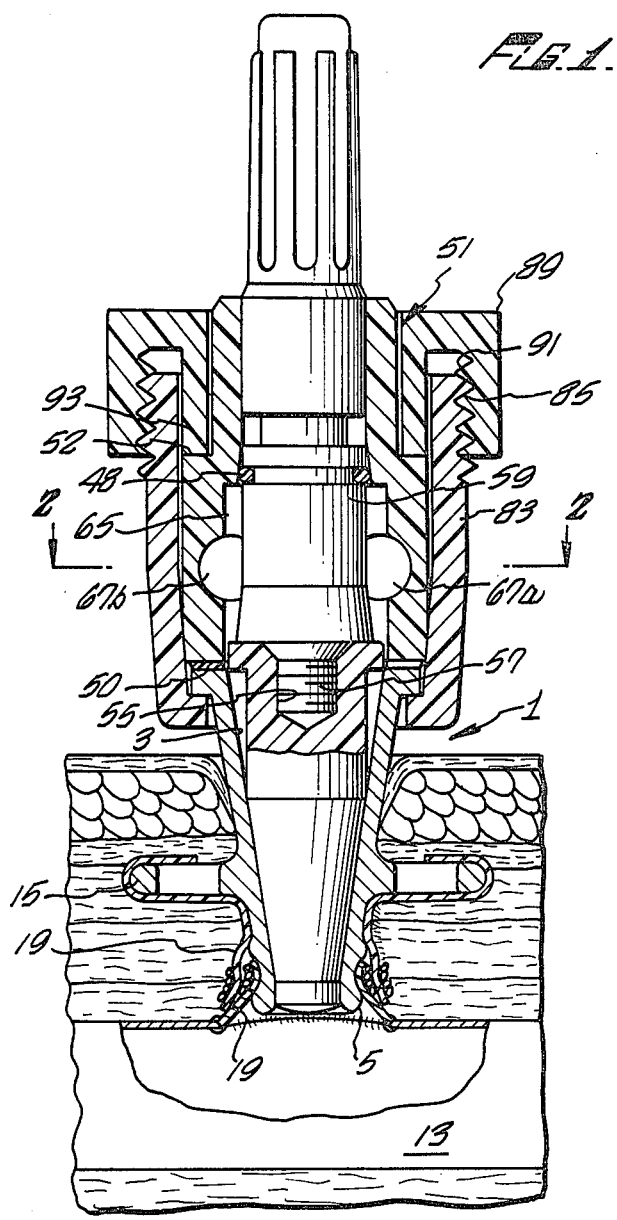
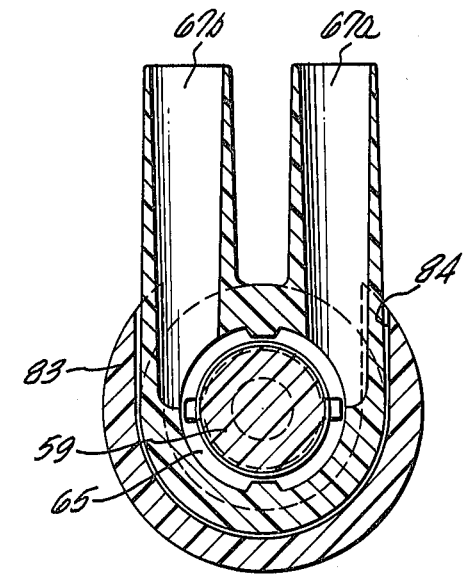
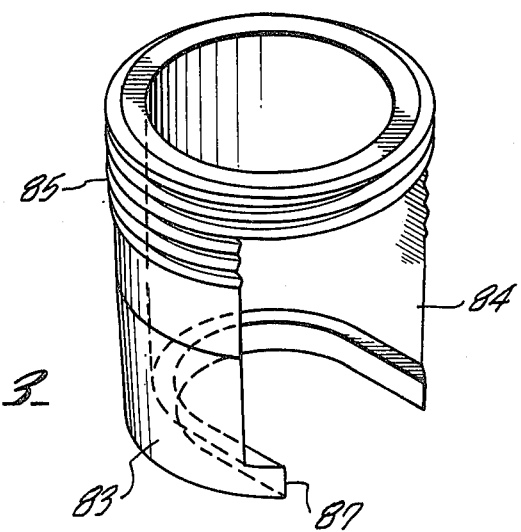

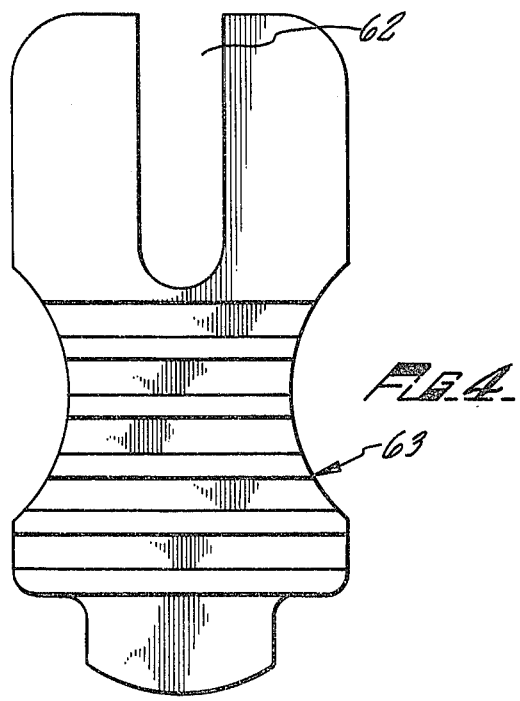
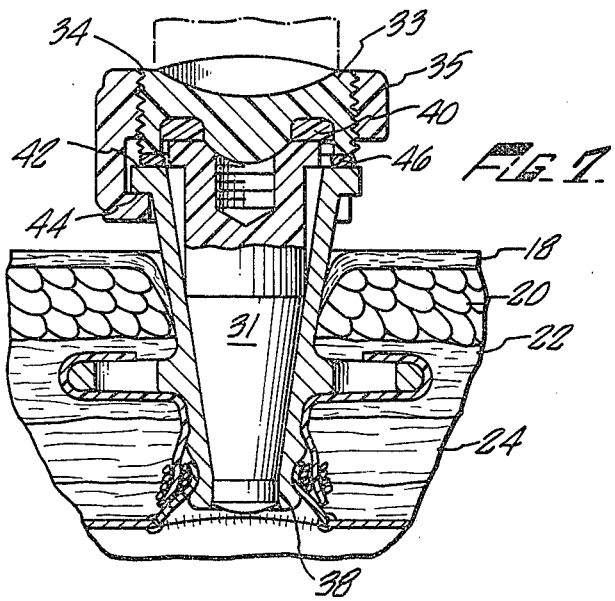
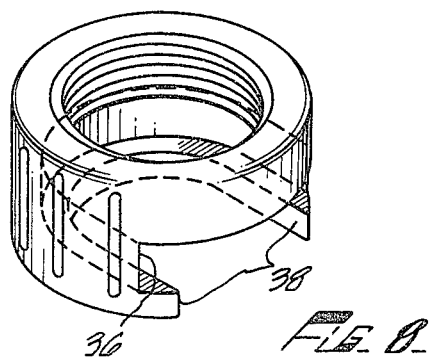
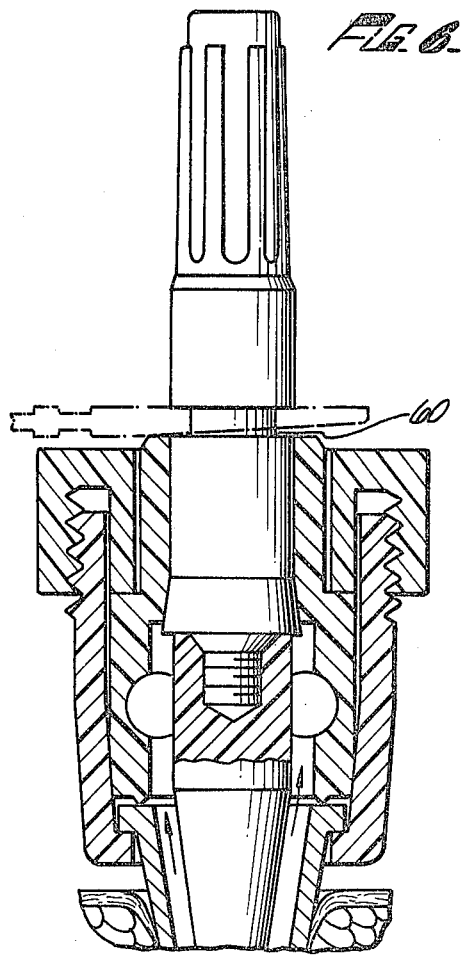

ATRAUMATIC BLOOD ACCESS DEVICE VALVE

BACKGROUND OF THE INVENTION

The present invention relates to a blood access device and its method of implantation.

There are a number of situations in which it is necessary to provide for fluid communication with the vascular system. For example, patients suffering from kidney failure require the dialysis of their blood by means external from the body. Blood containing toxic substances, such as urea, uric acid, creatine, phosphorus and calcium, must be removed from the blood system, treated and then returned to the patient. Patients requiring such blood dialysis need treatment at least two or three times per week. Patients suffering from hypoalimentation require a device for providing access to the body's vascular system on at least a daily basis.

One prior method of providing fluid communication with the vascular system involved the insertion of a needle into an artery from which blood to be treated was taken, and the insertion of a needle into a patient's view for blood return. Such a method proved unsatisfactory due to the difficulty in providing for the healing of the artery upon removal of the needle and the trauma produced by the repeated needle insertions. Such shortcomings led to the development of external, and later, internal shunts.

An external shunt involves the insertion of tubes, such as those made of Teflon, into an artery and an adjacent vein in a limb and providing an external communication or shunt between the tubes, which extends from the body of the patient. The shunt between the tubes is required in order to provide flow through the tubes during that period of time that access is not required for blood treatment. Were such circulating blood flow not provided, a blood clot or thrombus could form, as would be the case if the tubes were simply capped creating a static blood volume when the tubes were not in use. Dialysis, for example, is accomplished by connecting the arterial and venous tubing to a suitable dialysis unit. Such an external shunt configuration traumatizes the skin adjacent the Teflon tubes and a path is provided through the skin for infection to enter the patient's body. Furthermore, even with external shunts, blood clots sometimes form within the tubes and create a health hazard to the patient.

The disadvantages of external shunts led to the development of the internal shunt. An internal shunt is performed by joining, within a body, openings between an artery and an adjacent vein. The pressure in the artery being substantially greater than that in the vein causes the vein to become distended, forming a fistula. One or two needles are then inserted into the fistula in order to achieve communication with the patient's vascular system. The patient suffers major discomfort and pain each time the needles are inserted into the fistula. Moreover, the continuous insertions into the fistula cause it to become layered with scar tissue which ultimately prevents further intrusion, thus requiring the formation of another shunt.

Both the internal and external shunts increase the loading on the patient's heart due to the joining of the artery to a vein having a lower pressure, thereby lowering the artery's pressure, and requiring the heart to attempt to regain the original arterial blood pressure. Further, in many cases, the reduced circulation in the distal portion of the limb wherein the shunt is effected impairs the adequate removal of waste products from the muscles and other tissues resulting in weakness of the limb.

An object of the present invention is to provide an atraumatic valve for a blood access device. Other objects and advantages of this invention will become apparent upon a reading of the entire specification, including the drawings and claims.

DESCRIPTION OF THE DRAWINGS

FIG. 1 is a side view in partial cross-section, illustrating the present invention;

FIG. 2 is a cross-sectional view taken about 2—2 of FIG. 1;

FIGS. 3, 4, 5 and 8 are pictorial views illustrating a portion of the present invention; and FIGS. 6 and 7 are side views, in partial cross-section, illustrating the present invention.

SUMMARY OF THE INVENTION

The present invention provides for a valve and its method of use in a blood access device which has been permanently implanted through a patient's skin in order to provide access to the patient's vascular system while enabling full circulation throughout the vascular system as no external or internal shunt is required. The device and method of operation may also be utilized for patients which have had an internal shunt operation. After a blood access device has been implanted within a patient's body providing access to a blood vessel of the patient's vascular system, the present invention provides for the atraumatic opening and closing of a valve within the blood access device allowing for blood treatment without trauma to the patient's blood or body tissues surrounding the blood access device.

The valving mechanism of this invention includes a valve chamber which may be connected to that portion of the blood access device blood passageway which is positioned outside the body. The valve includes means for gently withdrawing and reinserting a plugging means positioned within the valve passageway in order to allow for blood flow therethrough. When the plugging means is positioned in its closed configuration, the blood within the blood passageway is substantially expelled into the body's vascular system, therefore minimizing the possibility of infection and the formation of blood clots.

More particularly, the present invention relates to a valving mechanism for use within a blood passageway of a blood access device. The valving mechanism includes a plugging means and a valve chamber for receiving the plugging means when it is removed from the blood passageway. The valving mechanism includes a retaining element adapted to slidably engage the valve chamber and an external rim of the blood access device for securing the valve chamber and blood access device. When the valve chamber is not in use, a retaining cap and cap retaining ring are used to secure the plugging means within the blood access device passageway.

DESCRIPTION OF PREFERRED EMBODIMENTS

Referring now to FIG. 1, the blood access device within which the atraumatic valving mechanism of this invention operates, will be discussed. The blood access device, generally referred to as 1, includes a blood passageway 3 having an external rim or lip 7, an anchor flange 15 and a flange means 5. The flange means 5 is secured to a blood vessel 13 by means of suitable surgical suture fiber 11.

FIG. 1 further illustrates the use of vascular grafting material 19 which both provides for the minimizing of blood loss during implantation surgery and provides structural support for tissue ingrowth which allows the blood vessel 13 and body tissues to be securely anchored to the blood access device 1. In a preferred embodiment the vascular grafting material is made of a Dacron, or a like fabric, and is impregnated with collagen. FIG. 7 illustrates a patient's skin 18, fat 20, fascia 22 and muscle 24 within which the blood access device 1 is anchored. A plugging means 31 is shown positioned within the blood passageway 3 of the blood access device 1 and is adapted to prevent blood flow therethrough and to expel blood from the blood passageway 3 upon insertion. The blood passageway is preferably tapered as illustrated in FIG. 1, the taper having an untapered portion along its tapered length as shown as a vertical ring 38 in FIG. 1 in order to provide an improved seal between the plugging means 31 and the blood passageway 3. The plugging means 31 is preferably restrained within the blood passageway 3 by means of a cap means 33 having a slot 34 at the top thereof and a threaded retaining ring 35. As shown in FIGS. 7 and 8, the retaining ring 35 is provided with an aperature 36 and a restraining shoulder 38 for sliding onto blood access device 1 and engaging external rim or lip 7 for a secure seal. As retaining ring 35 is threaded onto cap means 33, the base 40 of cap means 33 engages the upper portion 42 of external rim 7 and its restraining shoulder 38 engages the lower portion 44 of the external rim in an opposing direction. Porous washer 40, which may be a foamed polyurethane or polyethylene positioned between cap means 33 and upper portion of the plugging means 31 is preferably impregnated with an antiseptic such as betadyne. Sealing members 46, 48 and 50 provide for sealing between cap means 33 and upper portion 42 of rim 7, between stem member 59 and valve chamber 51, and between valve chamber 51 and external rim 7, respectively.

Having briefly described the blood access device with which the subject matter of this invention is utilized, the valving mechanism of this invention will now be more fully discussed.

When it is desired to remove blood from a patient's vascular system, restraining ring 35 is unthreaded, thereby allowing cap means 33 to be removed. A connector or valve chamber generally referred to as 51 may be positioned about the external rim or lip 7 of the blood access device 1 and retained in such a position by retaining element 83. The valve chamber 51 is preferably provided with an engaging lip 53 which mates with ring 7 of the blood access device 1.

In accordance with this invention, plugging means 31 is provided with an internally threaded aperature 55 adapted to engage the threaded portion 57 of a reciprocable stem member 59. The valve chamber 51 is further provided with a cavity portion 65 adapted to receive at least a portion of the plugging means 31 when said stem member 59 and connected plugging means 31 are pulled from said blood passageway 3 so as to allow blood flow from the blood vessel 13 through the blood passageway 3.

The retaining element 83 is provided with an aperature 84 which allows the retaining element to slide into place about the valve chamber 51. The retaining element 83 further includes external threads 85 and a restraining shoulder 87 adapted to engage external rim 7 of blood access device 1. Restraining element ring 89 is adapted to engage the shoulder 52 of valve chamber 51 with retaining ring member 93. Internal threads 91 of retaining ring 89 allow for the vice-like securing of the valve chamber 51 to blood access device 1. As the retaining element ring 89 is threaded onto retaining element 83, as illustrated in FIG. 1, retaining ring member 93 bears down on valve chamber shoulder 52 and restraining shoulder 87 exerts an opposing upward force on the external rim on lip 7 of blood access device 1.

Reciprocable stem member 59 includes an annular slot 60 which corresponds to the top of the valve chamber 51 when the reciprocable stem 59 is withdrawn in order to open the blood access device valves as shown in FIG. 6. When the reciprocable stem member 59 is in such positon, the slotted aperature 62 of tool 63 can be positioned about annular slot 60 in order to lock the reciprocable stem member in the open position. The opposed end 64 of the tool 63 is adapted to engage slot 34 of cap means 33 in order to assist in securing or removing the cap means 33.

While the preferred embodiments and the application of this invention have been shown and described, it will be apparent to those skilled in the art that modifications thereto may be made without departing from the inventive concepts herein described. The invention is, therefore, to be limited only by the scope of the claims appended hereto.

What is claimed is:

1. An atraumatic valving mechanism for operation within a blood passageway of a blood access device having an external rim, said blood passageway adapted to connect a blood vessel within a body to the body exterior, said valving mechanism comprising:
    a plugging means for sealing said blood passageway;
    a reciprocable stem member means for connection to said plugging means;
    a valve chamber means adapted to be secured to the portion of said blood access device blood passageway at said body exterior, said valve chamber including an aperature through which said reciprocable stem member means for connection to said plugging means may be passed and;
    a retaining element and a retaining element ring for engaging therewith for securing said valve chamber means to said blood access device, said retaining element having an aperature for slidably engaging said valve chamber and a restraining shoulder for engaging said blood access device external rim and forcing, from opposed directions, said valve chamber and blood access device together upon engaging said retaining element and retaining element ring.

2. The atraumatic valving mechanism claimed in claim 1 wherein;
    said stem member is further defined as having a threaded portion adapted to be inserted within an internally threaded portion of said plugging means.

3. The atraumatic valving mechanism claimed in claim 1 wherein;
    said valve chamber includes a blood inlet and a blood outlet.

4. An atraumatic valving mechanism for operation within a blood passageway of a blood access device, said blood passageway adapted to connect a blood vessel within a body to the body exterior, said valving mechanism comprising:

a plugging means for sealing said blood passageway;

a reciprocable stem member means for connection to said plugging means;

a valve chamber means adapted to be secured to the portion of said blood access device blood passageway at said body exterior, said valve chamber including a valve chamber shoulder and an aperature through which said reciprocable stem member means for connection to said plugging means may be passed and;

a retaining element and a retaining ring for engaging therewith securing said valve chamber means to said blood access device, said retaining ring having a member for engaging said valve chamber shoulder and forcing said valve chamber and said blood access device together upon engaging said retaining element and retaining element ring.

5. The atraumatic valving mechanism claimed in claim 4 wherein:

said stem member is further defined as having a threaded portion adapted to be inserted within an internally threaded portion of said plugging means.

6. The atraumatic valving mechanism claimed in claim 9 wherein;

said valve chamber further includes a blood inlet and a blood outlet.

7. An atraumatic valving mechanism for operation within a blood passageway of a blood access device, having an external rim, said blood passageway adapted to connect a blood vessel within a body to the body exterior, said valving mechanism comprising:

a plugging means for sealing said blood passageway;

a reciprocable stem member means for connection to said plugging means;

a valve chamber means adapted to be secured to the portion of said blood access device blood passageway at said body exterior, said valve chamber including a blood outlet, a valve chamber shoulder, and an aperature through which said reciprocable stem member means for connection to said plugging means may be passed and;

a retaining element and a retaining ring for engaging therewith securing said valve chamber means to said blood access device, said retaining element having an aperature for slidably engaging said valve chamber and a restraining shoulder for engaging said blood access device external rim and said retaining ring having a member for engaging said valve chamber shoulder thereby forcing, in opposed directions on either side of said external rim, said valve chamber and said blood access device together upon engaging said retaining element and retaining element ring.

8. The atraumatic valving mechanism claimed in claim 7 wherein:

said stem member is further defined as having a threaded portion adapted to be inserted within an internally threaded portion of said plugging means.

9. The atraumatic valving mechanism claimed in claim 7 wherein;

said valve chamber further includes a blood inlet and a blood outlet.

10. The atraumatic valving mechanism claimed in claim 8 wherein said threaded portion adapted to be inserted within said internally threaded portion of said plugging means includes a slot corresponding to the outer surface of said valve chamber when said plugging means is disengaged from said blood access device thereby allowing blood flow therethrough for locking said plugging device in such disengaged position.

* * * * *